(12) United States Patent
Kerr et al.

(10) Patent No.: US 7,807,646 B1
(45) Date of Patent: *Oct. 5, 2010

(54) SHIP-DEFICIENCY TO INCREASE MEGAKARYOCYTE PROGENITOR PRODUCTION

(75) Inventors: William G. Kerr, Tampa, FL (US); Caroline Desponts, Tampa, FL (US); Lia Elena Perez, Tampa, FL (US)

(73) Assignee: University of South Florida, Tampa, FL (US)

( * ) Notice: Subject to any disclaimer, the term of this patent is extended or adjusted under 35 U.S.C. 154(b) by 24 days.

This patent is subject to a terminal disclaimer.

(21) Appl. No.: 10/904,667

(22) Filed: Nov. 22, 2004

Related U.S. Application Data

(60) Provisional application No. 60/481,677, filed on Nov. 20, 2003.

(51) Int. Cl.
*A61K 48/00* (2006.01)
(52) U.S. Cl. ............... 514/44; 536/24.5; 536/24.31; 536/24.1
(58) Field of Classification Search .............. None
See application file for complete search history.

(56) References Cited

U.S. PATENT DOCUMENTS

| | | | |
|---|---|---|---|
| 4,603,112 | A | 7/1986 | Paoletti et al. |
| 4,769,330 | A | 9/1988 | Paoletti et al. |
| 4,777,127 | A | 10/1988 | Suni et al. |
| 5,017,487 | A | 5/1991 | Stunnenberg et al. |
| 5,166,057 | A | 11/1992 | Palese et al. |
| 5,804,412 | A | 9/1998 | Gill et al. |
| 6,025,198 | A | 2/2000 | Bennett et al. |
| 6,090,621 | A | 7/2000 | Kavanaugh et al. |
| 6,117,850 | A | 9/2000 | Patchen et al. |
| 6,506,559 | B1 | 1/2003 | Fire et al. |
| 6,703,215 | B2 | 3/2004 | Erneux |
| 2002/0137711 | A1 | 9/2002 | Kerr |
| 2002/0165192 | A1 | 11/2002 | Kerr et al. |
| 2003/0114401 | A1 | 6/2003 | Bennett et al. |
| 2003/0143732 | A1* | 7/2003 | Fosnaugh et al. ........... 435/325 |
| 2003/0166282 | A1 | 9/2003 | Brown et al. |
| 2004/0072298 | A1 | 4/2004 | Sauvageau et al. |
| 2004/0235765 | A1 | 11/2004 | Kerr et al. |
| 2004/0259247 | A1 | 12/2004 | Tuschl et al. |
| 2005/0054103 | A1* | 3/2005 | Peled et al. ................. 435/455 |
| 2006/0223749 | A1* | 10/2006 | Desponts et al. .............. 514/12 |
| 2007/0224124 | A1 | 9/2007 | Kerr et al. |
| 2008/0076731 | A1 | 3/2008 | Kerr |

FOREIGN PATENT DOCUMENTS

| | | |
|---|---|---|
| EP | 0 345 242 A2 | 12/1989 |
| EP | 0 440 219 A1 | 8/1991 |
| GB | 2 200 651 | 8/1988 |
| WO | WO 89/01973 A2 | 3/1989 |
| WO | WO 91/02805 A2 | 3/1991 |
| WO | WO 92/06693 A1 | 4/1992 |
| WO | WO 97/10252 A1 | 3/1997 |
| WO | WO 97/12039 A2 | 4/1997 |
| WO | WO 99/32619 A1 | 7/1999 |
| WO | WO 02/24233 | 3/2002 |
| WO | WO 02/44321 * | 6/2002 |
| WO | WO 02/078614 A3 | 10/2002 |
| WO | WO 2009/042910 A2 | 4/2009 |

OTHER PUBLICATIONS

Pasquet et al. Phosphatidylinositol 3,4,5-triphosphate regulates CA2 entry via Btk in platelets and megakaryocytes without increasing phospholipase C activity. EMBO Journal. 2000. vol. 19, No. 12 : 2793-2802.*

Wang et al. Influence of SHIP on the NK repertoire and allogeneic bone marrow transplantation. Science 2002, vol. 295: 2094-2097.*

Ahmed et al. Cytokine induced expansion of human CD34+ stem/progenitor and CD34+/CD41+ early megakaryocytic marrow cells cultured on normal osteoblasts. Stem Cells 1999, vol. 17: 92-99.*

Helgason et al. Targeted disruption of SHIP leads to hemopoietic perturbations, lung pathology, and shortened life span. Genes and Development 1998, vol. 12; pp. 1610-1620.*

U.S. Appl. No. 10/605,452, filed Sep. 30, 2003, Kerr et al.

U.S. Appl. No. 10/709,801, filed May 28, 2004, Desponts et al.

Agrawal, S. "Antisense oligonucleotides: towards clinical trials" *TIBTECH*, 1996, 14:376-387.

Agrawal, S. and Kandimalla, E. "Antisense therapeutics: is it as simple as complementary base recognition?" *Molecular Med. Today*, 2000, 6:72-81.

Akagi, K. et al. "Cre-mediated somatic site-specific recombination in mice" *Nucleic Acids Res*, 1997; 25(9):1766-1773.

Bender, M.A. et al. "Description and targeted deletion of 5' hypersensitive site 5 and 6 of the mouse β-globin locus control region" *Blood*, 1998, 92:4394-4403.

Braasch, D.A. and Corey, D.R. "Novel antisense and peptide nucleic acid strategies for controlling gene expression" *Biochemistry*, 2002, 41(14):4503-4510.

Branch, A. "A good antisense molecule is hard to find" *Trends in Biochem.*, 1998, 23:45-50.

Cantley, L.C. et al. "Oncogenes and signal transduction" *Cell*, 1991, 64:281-302.

Chirila, T. et al. "The use of synthetic polymers for delivery of therapeutic antisense oligodeoxynucleotides" *Biomaterials*, 2002, 23:321-342.

Crooke, S.T. "Basic principles of antisense therapeutics" in Antisense Res. and Application, chapter 1, pp. 1-50, S. Crooke, Ed., Springer-Verlag, 1999.

Desponts, C. et al. "MHC class I inhibitory receptors on natural killer cells recruit SHIP in an attempt to control cell survival" *FASEB Journal*, Mar. 20, 2002, 16(4):A706, abstract.

(Continued)

*Primary Examiner*—Kimberly Chong
(74) *Attorney, Agent, or Firm*—Saliwanchik, Lloyd & Saliwanchik

(57) ABSTRACT

A method of increasing megakaryocytes and platelet numbers in a patient comprising the step of inhibiting SHIP expression, including SHIP's enzymatic activity and signaling functions, whereby normal blood clotting is induced.

3 Claims, 4 Drawing Sheets

OTHER PUBLICATIONS

Evans, D.J. et al. "An engineered poliovirus chimaera elicits broadly reactive HIV-1 neutralizing antibodies" *Nature*, 1989, 339:385-388.
Fisher-Hoch, S.P. et al. "Protection of rhesus monkeys from fatal Lassa fever by vaccination with recombinant vaccinia virus containing the Lassa virus glycoprotein gene" *PNAS*, 1989, 86:317-321.
Gewirtz. A.M. et al. "Facilitating oligonucleotide delivery: Helping antisense deliver on its promise" *Proc. Natl. Acad. Sci. USA*, 1996, 93:3161-3163.
Ghansah, T. et al. "A role for the SH2-containing inositol phosphatase in the biology of natural killer cells and stem cells" Activating and Inhibitory Immunoglobulin-like Receptors, 2001, pp. 129-140.
Ghansah, T. et al. "Target disruption of Src homology 2-containing 5' inositol phosphatase (SHIP) alters PI3K/AKT and MAPK signal transduction pathways in murine natural killer cells" *FASEB Journal*, Mar. 20, 2002, 16(4):A706, abstract.
Ghansah, T. et al. "The Src homology 2 containing inositol phosphatase is vital for the function and homeostatis of Natural Killer cells" *FASEB Journal*, Mar. 7, 2001, 15(4):A655, abstract.
Guzman, R.J. et al. "Molecular and cellular cardiology/receptors: efficient and selective adenovirus-mediated gene transfer into vascular neointima" *Circulation*, 1993, 88(6):2838-2848.
Hawkins, P.T. et al. "Platelet-derived growth factor stimulates synthesis of PtdIns(3,4,5)$P_3$ by activating a PtdIns(4,5)$P_2$3-OH kinase" *Nature*, 1992, 358:157-910.
Held, W. et al. "Transgenic expression of the Ly49A natural killer cell receptor confers class I major histocompatibility complex (MHC)-specific inhibition and prevents bone marrow allograft rejection" *J. Exp. Med.*, 1996, 184(5):2037-2041.
Helgason; C.D. et al. "Homeostasis and regeneration of the hematopoietic stem cell pool are altered in SHIP-deficient mice" *Blood*, 2003, 102(10):3541-3547.
Helgason, C.D. et al. "Targeted disruption of SHIP leads to hemopoietic perturbations, lung pathology, and a shortened life span" *Genes & Dev.*, 1998, 12(11):1610-1620.
Huber, M. et al. "The src homology 2-containing inositol phosphatase (SHIP) is the gatekeeper of mast cell degranulation" *Proc. Natl. Acad. Sci. USA*, 1998, 95(19):11330-11335.
Jefferson, A.B. et al. "Properties of type II inositol polyphosphate 5-phosphatase" *J. Biol. Chem.*, 1995, 270(16):9370-9377.
Jen, K-Y and Gewirtz, A.M. "Suppression of gene expression by targeted disruption of messenger RNA: Available options and current strategies" *Stem Cells*, 2000, 18:307-319.
Jolly, D. et al. "Viral vector systems for gene therapy" *Cancer Gene Therapy*, 1998, 1(1):51-64.
Kass-Eisler, A. et al. "Quantitative determination of adenovirus-mediated gene delivery to rat cardiac myocytes in vitro and in vivo" *PNAS*, 1993, 90:11498-11502.
Kerr, William G. et al., Critical Role for SHIP in engraftment of histo-incompatible stem cells, Oncology Research, 2001, 12:285.
Klippel, A. et al. "Membrane localization of phosphatidylinositol 3-kinase is sufficient to activate multiple signal-transducing kinase pathways" *Mol Cell. Biol.*, 1996, 16(8):4117-4127.
Koh, C. et al. "Augmentation of antitumor effects by NK cell inhibitory receptor blockade in vitro and in vivo" *Blood*, 2001, 97(10):3132-3137.
Kolls, J. et al. "Prolonged and effective blockade of tumor necrosis factor activity through adenovirus-mediated gene transfer" *PNAS*, 1994, 91:215-219.
Lanier, L.L. "NK cell receptors" *Annual Rev of Immunology*, 1998, 16:359-393.
Liu, L. et al. "The Src homology 2 (SH2) domain of SH2-containing inositol phosphatase (SHIP) is essential for tyrosine phosphorylation of SHIP, its association with Shc, and its induction of apoptosis" *J. Biol. Chem.*, 1997, 272:8983-8988.
Liu, Q. et al. "SHIP is a negative regulator of growth factor receptor-mediated PKB/Akt activation any myeloid cell-survival" *Genes & Dev.*, 1999, 13(7):786-791.
Liu, Q. et al. "The inositol polyphosphate 5-phosphatase SHIP is a crucial negative regulator of B cell antigen receptor signaling" *J. Exp. Med.*, 1998, 188(7):1333-1342.
Lotzova, E. et al. "Prevention of Rejection of Allogeneic Bone Marrow Transplants by NK-1.1 Anti Serum" *Transplantation*, 1983, 35(5):490-494.
Lucas, D.M. and Rohrschneider, L. "A novel spliced form of SH2-containing inositol phosphatase is expressed during myeloid development" *Blood*, 1999, 93(6):1922-1933.
Moody, J.L. et al. "Anemia, thrombocytopenia, leukocytosis, extramedullary hematopoiesis, and impaired progenitor function in Pten$^{+/-}$SHIP$^{-/-}$ mice: a novel model of myelodysplasia" *Blood*, 2004, 103:4503-4510.
Okada, H. et al. "Cutting edge: Role of the inositol phosphatase SHIP in B cell receptor-induced $Ca^{2+}$ oscillatory response" *J. Immunol.*, 1998, 161:5192-5132.
Overbaugh, J. et al. "Molecular cloning of a feline leukemia virus that induces fatal immunodeficiency disease in cats" *Science*, 1988, 239:906-910.
Palu, G. et al. "In pursuit of new developments for gene therapy of human diseases" *J. Biotech*, 1999, 68:1-13.
Pihl-Carey, K. "Disease drug fails in phase III" *BioWorld Today*, 1999, 10:1-2.
Poznansky, M. et al. "Gene transfer into human lymphocytes by a defective human immunodeficiency virus type 1 vector" *J. Virol.*, 1991, 65:532-536.
Ruggeri, L. et al. "Role of natural killer cell alloreactivity in HLA-mismatched hematopoietic stem cell transplantation" *Blood*, 1999, 94(1):333-339.
Sabin, A.B. and Boulger, L.R. "History of Sabin attenuated poliovirus oral live vaccine strains" *J. of Biol. Standardization*, 1973, 1:115-118.
Samulski, R.J. et al. "Helper-free stocks of recombinant adeno-associated viruses: normal integration does not require viral gene expression" *J. Vir.*, 1989, 63(9):3822-3828.
Stephens, L.R. et al. "Agonist-stimulated synthesis of phosphatidylinositol(3,4,5)-trisphosphate: a new intracellular signaling system?" *Biochim. Biophys Acta*, 1993, 1179:27-75.
Tamm, I. et al. "Antisense therapy in oncology: new hope for an old idea?" *The Lancet*, 2001, 358:489-497.
Tu. Z. et al. "Embryonic and hematopoietic stem cells express a novel SH2-containing inositol 5'-phosphatase isoform" *Blood*, 2001, 98(7):2028-2038.
Wang, C.Y. and Huang, L. "pH-sensitive immunoliposomes mediate target-cell-specific delivery and controlled expression of a foreign gene in mouse" *PNAS*, 1987, 84:7851-7855.
Wang, J-W. et al. "Influence of ZSHIP on the NK Repertoire and Allogeneic Bone Marrow Transplantation" *Science*, 2002, 295(5562):2094-2097.
Wolf, I et al. "Cloning of the genomic locus of mouse SH2 containing inositol 5-phosphatase (SHIP) and a novel 110-kDa splice isoform, SHIPδ" *Genomics*, 2000, 69(1):104-112.
Yokoyama, W.M. "Natural killer cell receptors" *Current Opin in Immunology*, 1998, 10(3):298-305.
U.S. Appl. No. 11/451,004, filed Jun. 12, 2006, Kerr et al.
Agrawal, N. et al. "RNA interference: biology, mechanism, and applications" *Microbiol. Mol. Biol. Rev.*, 2003, 67:657-685.
Bonetta, L. "RNAi: Silencing never sounded better" *Nature Methods*, 2004, 1(1):79-86.
Caplen, N.J. "RNAi as a gene therapy approach" *Expert Opin. Biol. Ther.*, 2003, 3:575-586.
Caplen, N.J. et al. "Specific inhibition of gene expression by small double-stranded RNAs in invertebrate and vertebrate systems" *PNAS*, 2001, 98(17):9742-9747.
Damen, J.E. et al. "The 145-kDa protein induced to associate with Shc by multiple cytokines is an inositol tetraphosphate and phosphatidylinositol 3,4,5-trisphosphate 5-phosphatase" *Proc. Natl. Acad. Sci. USA*, 1996, 93:1689-1693.
Elbashir, S. et al. "Duplexes of 21-nucleotide RNAs mediate RNA interference in cultured mammalian cells" *Nature*, 2001, 411:494-498.
Elbashir, S. et al. "RNA interference is mediated by 21- and 22-nucleotide RNAs" *Genes & Development*, 2001, 15:188-200.
Fire, A. et al. "Potent and specific genetic interference by double-stranded RNA in *Caenorhabditis elegans*" *Nature*, 1998, 391:806-811.

Harborth, J. et al. "Identification of essential genes in cultured mammalian cells using small interfering RNAs" *J. Cell Sci.*, Dec. 2001, 114(Pt. 24):4557-4565.

Liu, Q. et al. "Molecular cloning and chromosomal localization in human and mouse of the SH2-containing inositol phosphatase, INPP5D (SHIP)" *Genomics*, 1997, 39:109-112.

Montgomery, M.K. et al. "RNA as a target of double-stranded RNA-mediated genetic interference in *Caenorhabditis elegans*" *Proc. Natl. Acad. Sci. USA*, 1998, 95:15502-15507.

Svoboda, P. et al. "Selective reduction of dormant maternal mRNAs in mouse oocytes by RNA interference" *Development*, 2000, 127:4147-4156.

Tuschl, T. et al. "RNA interference and small interfering RNAs" *Chembiochem*, 2001, 2(4):239-245.

Tuschl, T. et al. "Targeted mRNA degradation by double-stranded RNA in vitro" *Genes & Development*, 1999, 13:3191-3197.

Ware, M.D. et al. "Cloning and characterization of human SHIP, the 145-kD inositol 5-phosphatase that associates with SHC after cytokine stimulation" *Blood*, 1996, 88:2833-2840.

Zamore, P. et al. "RNAi: double-stranded RNA directs the ATP-dependent cleavage of mRNA at 21 to 23 nucleotide intervals" *Cell*, 2000, 101:25-33.

Hannon, G.J. and Rossi, J.J. "Unlocking the potential of the human genome with RNA interference" *Nature*, 2004, 431:371-378.

Hemann, M.T. et al. "An epi-allelic series of p53 hypomorphs created by stable RNAi produces distinct tumor phenotypes in vivo" *Nature Genetics*, 2003, 33:396-400.

Opalinska, J.B. and Gewirtz, A.M. "Nucleic-acid therapeutics: Basic principles and recent applications" *Nature Reviews*, 2002, 1:503-514.

Pera, M.F. et al. "Human embryonic stem cells" *J. Cell Sci.*, 2000, 113:5-10.

Puente, X.S. et al. "Human and mouse proteases: A comparative genomic approach" *Nature Reviews*, 2003, 4:544-558.

Rauh, M.J. et al. "The role of SHIP1 in macrophage programming and activation" *Biochem. Soc. Trans.*, 2004, 32:785-788.

Rehli, M. et al. "The membrane-bound ectopeptidase CPM as a marker of macrophage maturation in vitro and in vivo" *Adv. Exp. Med. Biol.*, 2000, 477:205-216.

Rohrschneider, L.R. et al. "Structure, function, and biology of SHIP proteins" *Genes & Develop.*, 2000, 14:505-520.

Verfaillie, C.M. "Hematopoietic stem cells for transplantation" *Nature Immunology*, 2002, 3:314-317.

Zandstra, P.W. et al. "Leukemia inhibitory factor (LIF) concentration modulates embryonic stem cell self-renewal and differentiation independently of proliferation" *Biotechnol. Bioeng.*, 2000, 69:607-617.

Examination Report dated Nov. 11, 2006, issued in related European application No. 01973144.7.

Ghansah, T. et al. "Expansion of myeloid suppressor cells in SHIP-deficient mice represses allogeneic T cell responses" *J. Immunology*, 2004, 173:7324-7330.

U.S. Appl. No. 11/451,004, filed Jun. 12, 2006, Kerr et al.

Kerr, W.G. et al. "The SH2 Containing Inositol Phosphatase (SHIP) is a Crucial Regulator of NK Cell Repertoire and Function" Abstract #34, presented at Core Research for Evolutional Science and Technology (CREST) International Symposium on Immunoglobulin-like Receptors, held Sep. 19-20, 2000, at the Sendai International Center, Sendai City, Japan.

Statement of Dr. Toshiyuki Takai, an organizer of the CREST International Symposium on Immunoglobulin-like Receptors, held Sep. 19-20, 2000.

Program and Abstracts for CREST International Symposium on Immunoglobulin-like Receptors, held Sep. 19-20, 2000.

Adams, "RNA Therapeutics Enter Clinical Trials" *The Scientist*, 2005, 19(1): 1-4.

Bjorklund L.M. "Embryonic Stem Cells Develop into Functional dopaminergic neurons after transplantation in a Parkinson rat model" *PNAS*, 2002, 99: 2344-2349.

Geier, et al. "The Human SHIIP Gene is Differentially Expressed in Cell Lineages of the Bone Marrow and Blood" *J Blood*, 1997, 89: 1876-1885.

Hemmati-Brivanlou et al. "Vertebrate Embryonic Cells Will Become Nerve Cells Unless Told Otherwise" *Cell*, 1997, 88: 13-17.

Kawasaki, et al. "Induction of Midbrain Dopaminergic Neurotechnique Neurons from ES Cells by Stromal Cell-Derived Inducing Activity" *Neuron*, 2000, 28:31-40.

Kim, et al. "Dopamine Neurons derived from embryonic stem cells function in an animal model of Parkinson's disease" *Nature*, 2002, 418: 50-56.

Novina, et al. "The RNAi revolution" *Nature*, 2004, 430: 161-164.

Paroo, et al. "Challenges for RNAi in vivo" *Trends in Biotechnology*, 2004, 22(8): 390-394.

Peracchi, A. "Prospects for antiviral ribozymes and deoxyribozymes" *Rev Med Virol*, 2004, 14: 47-64.

Office Action mailed Jan. 14, 2009 in U.S. Appl. No. 09/955,174.

Office Action mailed Jan. 7, 2009 in U.S. Appl. No. 10/904,667.

Office Action mailed Dec. 16, 2008 in U.S. Appl. No. 11/787,064.

Office Action mailed Sep. 22, 2008 in U.S. Appl. No. 10/709,801.

Office Action mailed Aug. 5, 2008 in U.S. Appl. No. 11/451,004.

Bolland, S. et al. "Ship Modulates Immune Receptor Responses by Regulating Membrane Association of Btk" *Immunity*, Apr. 1998, pp. 509-516, vol. 8.

De Souza, A.T. et al. "Transcriptional and phenotypic comparisons of Ppara knockout and siRNA knockdown mice" *Nucleic Acids Research*, 2006, pp. 4486-4494, vol. 34, No. 16.

Huber, M. et al. "The role of SHIP in growth factor induced signalling" *Progress in Biophysics & Molecular Biology*, 1999, pp. 423-434, vol. 71.

Krystal, G. et al. "Molecules in focus: SHIPs ahoy" *The International Journal of Biochemistry & Cell Biology*, 1999, pp. 1007-1010, vol. 31.

Muraille, E. et al. "Distribution of the Src-homology-2-domain-containing inositol 5-phosphatase SHIP-2 in both non-haemopoietic and haemopoietic cells and possible involvement of SHIP-2 in negative signaling of B-cells" *Biochem J*, 1999, pp. 697-705, vol. 342.

Novina, C.D. et al. "The RNAi revolution" Nature, Jul. 8, 2004, pp. 161-164, vol. 430.

Odorico, J.S. et al. "Multilineage Differentiation from Human Embryonic Stem Cell Lines" Stem Cells, 2001, pp. 193-204, vol. 19.

Perez, L.E. et al. "$SH_2$-Inositol Phosphatase 1 Negatively Influences Early Megakaryocyte Progenitors" *PLOS One*, Oct. 2008, 3(10):e3565, pp. 1-8.

Sawyers, C.L. "Chronic Myeloid Leukemia" The New England Journal of Medicine, Apr. 29, 1999, pp. 1330-1340, vol. 340, No. 17.

Sly, L.M. et al. "SHIP, SHIP2, and PTEN activities are regulated in vivo by modulation of their protein levels: SHIP is up-regulated in macrophages and mast cells by lipopolysaccharide" *Experimental Hematology*, 2003, pp. 1170-1181, vol. 31.

Wang, J.W. et al. Identification of a Novel Lipopolysaccharide-Inducible Gene with Key Features of Both a Kinase Anchor Proteins and chs1/beige Proteins, *The Journal of Immunology*, 2001, 166:4586-4595.

Wisniewski, D. et al. "Neoplasia: A Novel SH2-Containing Phosphatidylinositol 3,4,5-Trisphosphate 5-Phosphatase (SHIP2) Is Constitutively Tyrosine Phosphorylated and Associated With src Homologous and Collagen Gene (SHC) in Chronic Myelogenous Leukemia Progenitor Cells" *Blood*, Apr. 1999, pp. 2707-2720, vol. 93, No. 8.

Zwaka, T.P. et al. "Homologous recombination in human embryonic stem cells" Nature Biotechnology, Feb. 10, 2003, pp. 1-3, doi: 10.1038/nbt788, advance online publication.

Office Action mailed Apr. 28, 2009 in U.S. Appl. No. 10/709,801, filed May 28, 2004.

Office Action mailed Sep. 28, 2009 in U.S. Appl. No. 11/451,004, filed Jun. 12, 2006.

Office Action mailed Apr. 7, 2009 in U.S. Appl. No. 11/451,004, filed Jun. 12, 2006.

Office Action mailed Jun. 5, 2009 in U.S. Appl. No. 11/787,064, filed Apr. 13, 2007.

Office Action mailed Feb. 10, 2006 in U.S. Appl. No. 10/097,101, filed Feb. 14, 2002.

Office Action mailed Oct. 17, 2006 in U.S. Appl. No. 10/605,452, filed Sep. 30, 2003.

Pesesse, X. et al. "The SH2 domain containing inositol 5-phosphatase SHIP2 displays phosphatidylinositol 3,4,5-trisphosphate and inositol 1,3,4,5-tetrakisphosphate 5-phosphatase activity" *FEBS Letters*, 1998, pp. 301-303, vol. 437.

U.S. Appl. No. 12/670,360, Kerr et al.

U.S. Appl. No. 12/689,167, Desponts et al.

U.S. Appl. No. 12/651,809, Kerr.

\* cited by examiner

SEQUENCE LISTING

```
<160> NUMBER OF SEQ ID NOS: 1

<210> SEQ ID NO 1
<211> LENGTH: 4870
<212> TYPE: DNA
<213> ORGANISM: Human

<400> SEQUENCE: 1
gtggaggggc ctccgctccc ctcggtggtg tgtgggtcct gggggtgcct gccggcccag      60
ccgaggaggc ccacgcccac catggtcccc tgctggaacc atggcaacat cacccgctcc     120
aaggcggagg agctgctttc caggacaggc aagggcacga gcttcctcgt gcgtgccagc     180
gagtccatct cccgggcata cgcgctctgc gtgctgtatc ggaattgcgt ttacacttac     240
agaattctgc ccaatgaaga tgataaattc actgttcagg catccgaagg cgtctccatg     300
aggttcttca ccaagctgga ccagctcatc gagtttttaca agaaggaaaa catggggctg     360
gtgacccatc tgcaataccc tgtgccgctg gaggaagagg acacaggcga cgaccctgag     420
gaggacacag tagaaagtgt cgtgtctcca cccgagctgc ccccaagaaa catcccgctg     480
actgccagct cctgtgaggc caaggaggtt ccttttttcaa acgagaatcc ccgagcgacc     540
gagaccagcc ggccgagcct ctccgagaca ttgttccagc gactgcaaag catggacacc     600
agtgggcttc cagaagagca tcttaaggcc atccaagatt atttaagcac tcagctcgcc     660
caggactctg aatttgtgaa gacagggtcc agcagtcttc ctcacctgaa gaaactgacc     720
acactgctct gcaaggagct ctatggagaa gtcatccgga ccctcccatc cctggagtct     780
ctgcagaggt tatttgacca gcagctctcc ccgggcctcc gtccacgtcc tcaggttcct     840
ggtgaggcca atcccatcaa catggtgtcc aagctcagcc aactgacaag cctgttgtca     900
```

```
tccattgaag acaaggtcaa ggccttgctg cacgagggtc ctgagtctcc gcaccggccc    960
tcccttatcc ctccagtcac ctttgaggtg aaggcagagt ctctggggat tcctcagaaa   1020
atgcagctca aagtcgacgt tgagtctggg aaactgatca ttaagaagtc caaggatggt   1080
tctgaggaca agttctacag ccacaagaaa atcctgcagc tcattaagtc acagaaattt   1140
ctgaataagt tggtgatctt ggtggaaaca gagaaggaga agatcctgcg gaaggaatat   1200
gttttttgctg actccaaaaa gagagaaggc ttctgccagc cctgcagca gatgaagaac   1260
aagcactcag agcagccgga gcccgacatg atcaccatct tcatcggcac ctggaacatg   1320
ggtaacgccc cccctcccaa gaagatcacg tcctggtttc tctccaaggg gcagggaaag   1380
acgcgggacg actctgcgga ctacatcccc catgacattt acgtgatcgg cacccaagag   1440
gaccccctga gtgagaagga gtggctggag atcctcaaac actccctgca agaaatcacc   1500
agtgtgactt ttaaaacagt cgccatccac acgctctgga acatccgcat cgtggtgctg   1560
gccaagcctg agcacgagaa ccggatcagc cacatctgta ctgacaacgt gaagacaggc   1620
attgcaaaca cactgggaa caaggggagc gtgggggtgt cgttcatgtt caatggaacc   1680
tccttagggt tcgtcaacag ccacttgact tcaggaagtg aaaagaaact caggcgaaac   1740
caaaactata tgaacattct ccggttcctg gccctgggcg acaagaagct gagtcccttt   1800
aacatcactc accgcttcac gcacctcttc tggtttgggg atcttaacta ccgtgtggat   1860
ctgcctacct gggaggcaga accatcatc cagaaaatca gcagcagca gtacgcagac   1920
ctcctgtccc acgaccagct gctcacagag aggagggagc agaaggtctt cctacacttc   1980
gaggaggaag aaatcacgtt tgccccaacc taccgttttg agagactgac tcgggacaaa   2040
tacgcctaca ccaagcagaa agcgacaggg atgaagtaca acttgccttc ctggtgtgac   2100
cgagtcctct ggaagtctta tcccctggtg cacgtggtgt gtcagtctta tggcagtacc   2160
agcgacatca tgacgagtga ccacagccct gtctttgcca catttgaggc aggagtcact   2220
tcccagtttg tctccaagaa cggtcccggg actgttgaca gccaaggaca gattgagttt   2280
ctcaggtgct atgccacatt gaagaccaag tcccagacca aattctacct ggagttccac   2340
tcgagctgct tggagagttt tgtcaagagt caggaaggag aaaatgaaga aggaagtgag   2400
ggggagctgg tggtgaagtt tggtgagact cttccaaagc tgaagcccat tatctctgac   2460
cctgagtacc tgctagacca gcacatcctc atcagcatca agtcctctga cagcgacgaa   2520
tcctatggcg agggctgcat tgcccttcgg ttagaggcca cagaaacgca gctgcccatc   2580
tacacgcctc tcacccacca tgggggagttg acaggccact tccaggggga gatcaagctg   2640
cagacctctc agggcaagac gagggagaag ctctatgact ttgtgaagac ggagcgtgat   2700
gaatccagtg ggccaaagac cctgaagagc ctcaccagcc acgaccccat gaagcagtgg   2760
gaagtcacta gcagggcccc tccgtgcagt ggctccagca tcactgaaat catcaacccc   2820
aactacatgg gagtggggcc ctttgggcca ccaatgcccc tgcacgtgaa gcagaccttg   2880
tcccctgacc agcagcccac agcctggagc tacgaccagc cgcccaagga ctcccgctg    2940
gggccctgca ggggagaaag tcctccgaca cctcccggcc agccgcccat atcacccaag   3000
aagttttttac cctcaacagc aaaccggggt ctccctccca ggacacagga gtcaaggccc   3060
agtgacctgg ggaagaacgc aggggacacg ctgcctcagg aggacctgcc gctgacgaag   3120
cccgagatgt ttgagaaccc cctgtatggg tccctgagtt ccttccataa gcctgctccc   3180
aggaaggacc aggaatcccc caaaatgccg cggaaggaac ccccgccctg cccggaaccc   3240
```

```
ggcatcttgt cgcccagcat cgtgctcacc aaagcccagg aggctgatcg cggcgagggg    3300
cccggcaagc aggtgcccgc gccccggctg cgctccttca cgtgctcatc ctctgccgag    3360
ggcagggcgg ccggcgggga caagagccaa gggaagccca agaccccggt cagctcccag    3420
gccccggtgc cggccaagag gcccatcaag ccttccagat cggaaatcaa ccagcagacc    3480
ccgcccaccc cgacgccgcg gccgccgctg ccagtcaaga gccggcggt  gctgcacctc    3540
cagcactcca agggccgcga ctaccgcgac aacaccgagc tcccgcatca cggcaagcac    3600
cggccggagg aggggccacc agggcctcta ggcaggactg ccatgcagtg aagccctcag    3660
tgagctgcca ctgagtcggg agcccagagg aacggcgtga agccactgga ccctctcccg    3720
ggacctcctg ctggctcctc ctgcccagct tcctatgcaa ggctttgtgt tttcaggaaa    3780
gggcctagct tctgtgtggc ccacagagtt cactgcctgt gagacttagc accaagtgct    3840
gaggctggaa gaaaacgca  caccagacgg gcaacaaaca gtctgggtcc ccagctcgct    3900
cttggtactt gggacccag  tgcctcgttg agggcgccat tctgaagaaa ggaactgcag    3960
cgccgatttg agggtggaga tatagataat aataatatta ataataataa tggccacatg    4020
gatcgaacac tcatgatgtg ccaagtgctg tgctaagtgc tttacgaaca ttcgtcatat    4080
caggatgacc tcgagagctg aggctctagc cacctaaaac cacgtgccca aacccaccag    4140
tttaaaacgt tgtgtgttcg gaggggtgaa agcattaaga agcccagtgc cctcctggag    4200
tgagacaagg gctcggcctt aaggagctga agagtctggg tagcttgttt agggtacaag    4260
aagcctgttc tgtccagctt cagtgacaca agctgcttta gctaaagtcc cgcgggttcc    4320
ggcatggcta ggctgagagc agggatctac ctggcttctc agttctttgg ttggaaggag    4380
caggaaatca gctcctattc tccagtggag agatctggcc tcagcttggg ctagagatgc    4440
caaggcctgt gccaggttcc ctgtgccctc ctcgaggtgg gcagccatca ccagccacag    4500
ttaagccaag ccccccaaca tgtattccat cgtgctggta gaagagtctt tgctgttgct    4560
cccgaaagcc gtgctctcca tcctggctgc cagggagggt gggcctcttg gttccaggct    4620
cttgaaatag tgcagccttt tcttcctatc tctgtggctt tcaactctgc ttccttggtt    4680
attaagagaa tagatgggtg atgtctttcc ttatgttgct ttttcaacat agcagaatta    4740
atgttgggag ctaaatccac tggtgtgtgt gaatgcagaa gggaatgcac cccaccttcc    4800
catgaatgaa gtctgcgtac caataaattg tgccttctcc tccaaaaaaa aaaaaaaaaa    4860
ataaaaaaaa                                                         4870
```

US 7,807,646 B1

SHIP-DEFICIENCY TO INCREASE MEGAKARYOCYTE PROGENITOR PRODUCTION

STATEMENT OF GOVERNMENT INTEREST

The subject matter of this application has been supported by research grants from the Leukemia and Lymphoma Society of America and the National Institutes of Health under grant numbers HL072523 and CA087989. Accordingly, the government has certain rights in this invention.

REFERENCE TO RELATED APPLICATIONS

This invention is based on priority document U.S. Provisional Application titled, "Ship-Deficiency to Increase Megakaryocyte and Platelet Production," Application Ser. No. 60/481,677 filed on Nov. 20, 2003.

BACKGROUND OF INVENTION

Platelets are critical for blood clotting. However, in various human anemias, and in bone marrow transplant patients, platelets and the megakaryocytes they are derived from can drop below a critical threshold that is required to maintain normal clotting. This can require platelet transfusions that are very expensive and which place the patient at risk for infection by blood-borne pathogens (e.g. HIV, HepB and C).

Mice that lack expression of a SH2-domain-containing Inositol 5-Phosphatase (SHIP) gene exhibit increased levels of both megakaryocyte progenitors and megakaryocytes in the bone marrow and spleens. In fact, megakaryocytes, the immediate precursor of platelets, are increased in the periphery of SHIP deficient mice approximately 10-100 fold. Therefore, methods that inhibit SHIP expression, its enzymatic activity or its signaling functions could be used in human patients to temporarily increase megakaryocytes and platelet numbers during periods when their platelets drop below numbers sufficient to promote normal blood clotting. In a similar way, SHIP expression or activity could be used to increase the yield of megakaryocytes, megakaryocyte progenitors or platelets in ex vivo expansion regimens that use human growth factors.

SUMMARY OF INVENTION

The unexpected observations below provide the basis for this invention, which is directed to a method of increasing the yield of megakaryocytes through the inhibition of the SHIP gene.

Mice that lack expression of a SHIP gene exhibit increased levels of both megakaryocyte progenitors and megakaryocytes in the bone marrow and spleens. In fact, megakaryocytes, the immediate precursor of platelets, are increased in the periphery of SHIP deficient mice approximately 10-100 fold. Therefore, methods that inhibit SHIP expression, its enzymatic activity or its signaling functions could be used in human patients to temporarily increase megakaryocytes and platelet numbers during periods when their platelets drop below numbers sufficient to promote normal blood clotting. In a similar way, SHIP expression or activity could be used to increase the yield of megakaryocytes, megakaryocyte progenitors or platelets in ex vivo expansion regimens that use human growth factors.

In one embodiment, the instant invention discloses a method of increasing the yield of megakaryocytes in a patient, in vivo, comprising the steps of administering a therapeutically effective amount of a substance that inhibits SHIP function to the patient. The method wherein the function of SHIP is inhibited using a method chosen from the group consisting of RNA interference, antisense oligonucleotides, ribozymes, DNAzymes, nucleic acid modifiers, PNAs, nonstandard nucleic acids, aptamers, decoys, oligonucleotide based gene regulation, and dominant/negative mutants.

An alternate embodiment discloses a method of increasing the yield of megakaryocytes from a patient, ex vivo, comprising the steps of harvesting target cells from a patient and contacting the target cells with an efficacious amount of a substance that inhibits SHIP function. The function of SHIP is inhibited using a method chosen from the group consisting of RNA interference, antisense oligonucleotides, ribozymes, DNAzymes, nucleic acid modifiers, PNAs, nonstandard nucleic acids, aptamers, decoys, oligonucleotide based gene regulation, and dominant/negative mutants. Target cells are chosen from the group consisting of megakaryocytes, megakaryocyte progenitors, and platelets.

Another embodiment encompasses a method of improving haematopoietic recovery in a patient in need thereof, in vivo, comprising the step of administering a therapeutically effective amount of a substance that inhibits SHIP function to the patient. SHIP function is inhibited using a method chosen from the group consisting of RNA interference, antisense oligonucleotides, ribozymes, DNAzymes, nucleic acid modifiers, PNAs, nonstandard nucleic acids, aptamers, decoys, oligonucleotide based gene regulation, and dominant/negative mutants.

Alternatively, a method of improving haematopoietic recovery in a patient in need thereof, ex vivo, is disclosed comprising the steps of harvesting target cells from a patient, contacting the target cells with an efficacious amount of a substance that inhibits SHIP function, and reinfusing the expanded target cells into the patient. The target cells are chosen from the group consisting of megakaryocytes, megakaryocyte progenitors, and platelets.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
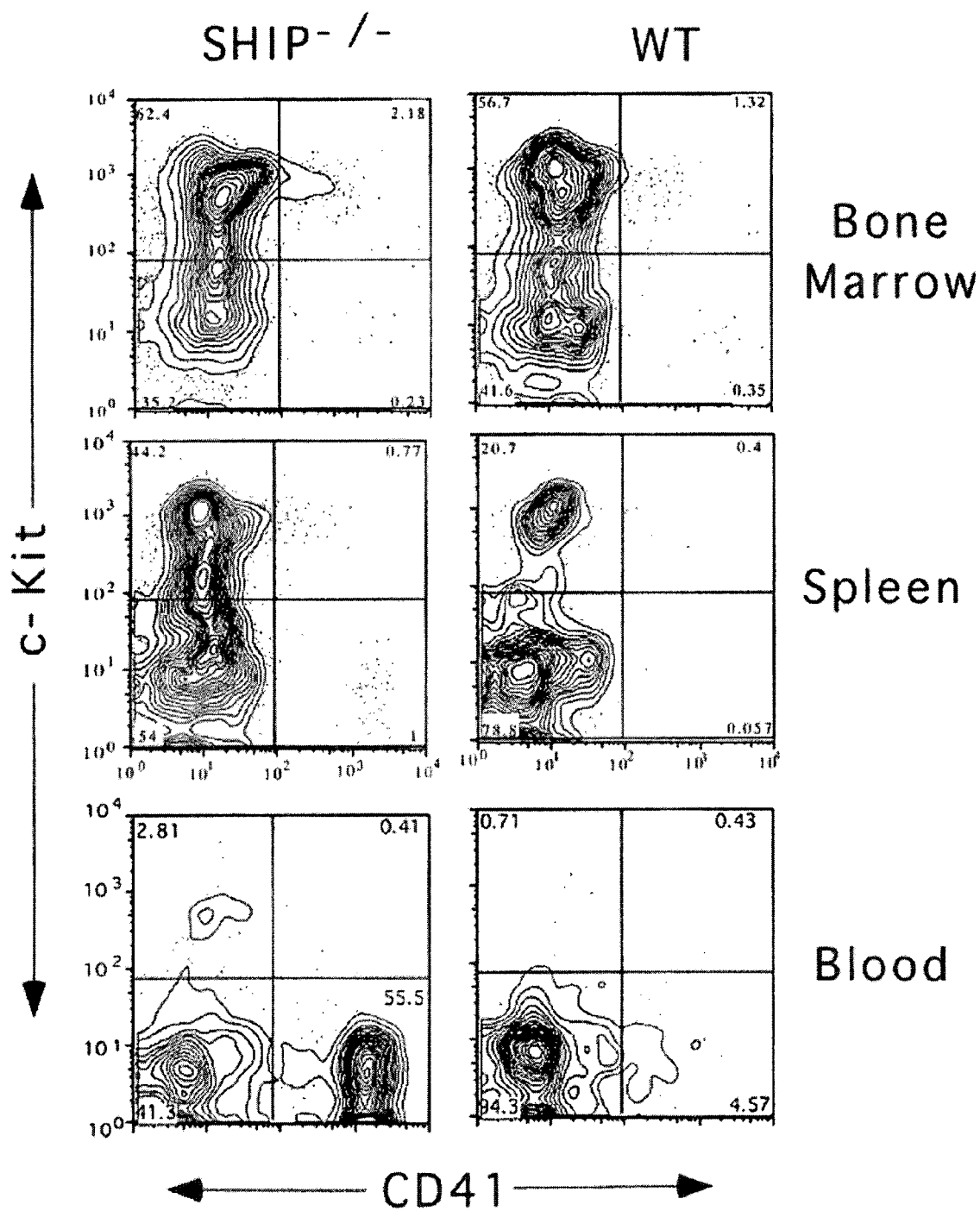
FIG. 1. SHIP1-deficiency increases the number of megakaryocytes (CD41+ c-kit−) and megakaryocyte progenitors (CD41+ c-kit+) in the hematopoietic compartment.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The invention is based on a method of modulating megakaryocytes, and their progenitors, as a significant leap forward in the treatment of various human anemias. The inventors reasoned that the identification of a novel gene involved in megakaryocyte production would lead to increased efficacy of current treatments. The clinical potential of such an approach is significant, as it allows for modulation of a gene specific determinate of megakaryocyte production.

The studies described below in Example I demonstrate that SHIP1-deficiency increases the number of megakaryocytes (CD41+ c-kit−) and megakaryocyte progenitors (CD41+ c-kit+) in the hematopoietic compartment. The study in Example II establishes that SHIP1-deficiency increases the number of circulating platelets. Example III demonstrates statistical analysis of increased megakaryocyte progenitors, megakaryocytes and platelets in SHIP-deficient (SHIP−/−) mice. The studies described in Example 4 provide evidence that SHIP1-deficiency increases the frequency of megakaryocyte progenitors and megakaryocytes in the hematopoietic compartment.

The term "gene of interest" or "target gene" refers to a nucleic acid which can be of any origin and isolated from a genomic DNA, a cDNA, or any DNA encoding a RNA, such as a genomic RNA, a mRNA, an anti-sense RNA, a ribosomal RNA, a ribozyme or a transfer RNA. The gene of interest can also be an oligonucleotide (i.e., a nucleic acid having a short size of less than 100 bp). It can be engineered from genomic DNA to remove all or part of one or more intronic sequences (i.e., minigene).

In one embodiment, the gene of interest in use in the present invention, SHIP1 (SEQ. ID. NO. 1), encodes a target gene product, such as a protein, of therapeutic interest. A gene product of therapeutic interest, or target gene protein, is one which has a therapeutic or protective activity when administered appropriately to a patient, especially a patient suffering from a disease or illness condition or who should be protected against this disease or condition. Such a therapeutic or protective activity can be correlated to a beneficial effect on the course of a symptom of said disease or said condition.

In the context of the invention, the gene of interest can be homologous or heterologous to the host cell into which it is introduced. Advantageously, it encodes a polypeptide, a ribozyme or an anti-sense RNA. The term "polypeptide" is to be understood as any translational product of a polynucleotide whatever its size is, and includes polypeptides having as few as 7 residues (peptides), but more typically proteins. In addition, it may be from any origin (prokaryotes, lower or higher eukaryotes, plant, virus etc). It may be a native polypeptide, a variant, a chimeric polypeptide having no counterpart in nature or fragments thereof. Advantageously, the gene of interest in use in the present invention encodes at least one polypeptide that can compensate for one or more defective or deficient cellular proteins in an animal or a human organism, or that acts through toxic effects to limit or remove harmful cells from the body. A suitable polypeptide may also be immunity conferring and acts as an antigen to provoke a humoral or a cellular response, or both.

The inventive method includes modulating the activity of a cell expressing one or more nucleic acids, operably linked to a gene of interest. The phrases "nucleic acid" or "nucleic acid sequence" as used herein refers to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

In general, the target nucleic acid is DNA. However, inventive methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for determination of the sensitivity of the target cells to radiation therapy may be extracted by a variety of techniques such as that described by Sambrook, et al. (Molecular Cloning: A Laboratory Manual, Cold Spring Harbor, N.Y., 1989; incorporated in its entirety herein by reference).

Cells expressing the target nucleic acid isolated from a subject can be obtained in a biological specimen from the subject. The cells, or nucleic acid, can be isolated from tumor tissue, brain tissue, cerebrospinal fluid, blood, plasma, serum, lymph, lymph nodes, spleen, liver, bone marrow, or any other biological specimen. Tumor tissue, blood, plasma, serum, lymph, brain tissue, cerebrospinal fluid and bone marrow are obtained by various medical procedures known to those of skill in the art.

The inventive methods are useful for producing a clinical response to treatment of various human anemias, bone marrow transplants, or cell proliferative disorders. A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is noncancerous, e.g. its cells do not invade surrounding tissues or metastasize to distant sites. The term "malignant" refers to a tumor that is metastatic, invades contiguous tissue or no longer under normal cellular growth control.

As used herein, "a clinical response" is the response of a subject to modulation of the gene of interest. Criteria for determining a response to therapy are widely accepted and enable comparisons of the efficacy alternative treatments (see Slapak and Kufe, Principles of Cancer Therapy, in Harrisons's Principles of Internal Medicine, 13th edition, eds. Isselbacher et al., McGraw-Hill, Inc. 1994). A complete response (or complete remission) is the disappearance of all detectable malignant disease. A partial response is an approximately 50 percent decrease in the product of the greatest perpendicular diameters of one or more lesions. There can be no increase in size of any lesion or the appearance of new lesions. Progressive disease means at least an approximately 25 percent increase in the product of the greatest perpendicular diameter of one lesion or the appearance of new lesions. The response to treatment is evaluated after the subjects had completed therapy.

Pharmaceutical Compositions

Target gene proteins, and anti-target gene antibodies, and modulators of the target gene expression or activity (also referred to herein as "active compounds") can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The target gene nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

Uses and Methods of the Invention

The target gene nucleic acid molecules, proteins, protein homologues, and antibodies described herein can be used in screening assays, predictive medicine (e.g., diagnostic assays, prognostic assays, monitoring clinical trials, and pharmacogenomics), and methods of treatment (e.g., therapeutic treatment methods and prophylactic treatment methods).

Screening Assays

The invention provides a method (also referred to herein as a "screening assay") for identifying modulators, i.e., candidate or test compounds or agents (e.g., peptides, peptidomimetics, small molecules or other drugs) which bind to the target gene proteins or have a stimulatory or inhibitory effect on, for example, the target gene expression or the target gene activity. Such identified compounds may be useful for the modulation of drug resistance. In one embodiment, the invention provides assays for screening candidate or test compounds which bind to or modulate the activity of the target gene protein or polypeptide or biologically active portion thereof. The test compounds of the present invention can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; and Felici (1991) J. Mol: Biol. 222:301-310).

In one embodiment, an assay is a cell-based assay in which a cell which expresses the target gene protein, or a biologically active portion thereof, is contacted with a test compound and the ability of the test compound to bind to the target gene protein determined. The cell, for example, can be a yeast cell or a cell of mammalian origin. Determining the ability of the test compound to bind to the target gene protein can be accomplished, for example, by coupling the test compound with a radioisotope or enzymatic label such that binding of the test compound to the target gene protein or biologically active portion thereof can be determined by detecting the labeled compound in a complex. For example, test compounds can be labeled with 125 I, 35 C, 14 C, or 3H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses the target gene protein, or a biologically active portion thereof, with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or a biologically active portion thereof as compared to the known compound.

In another embodiment, an assay is a cell-based assay comprising contacting a cell expressing the target gene protein, or a Biologically active portion thereof, with a test compound and determining the ability of the test compound to modulate (e.g., stimulate or inhibit) the activity of the target gene protein or biologically active portion thereof. Determining the ability of the test compound to modulate the activity of the target gene or a biologically active portion thereof can be accomplished, for example, by determining the ability of the target gene protein to bind to or interact with the target gene target molecule. As used herein, a "target molecule" is a molecule with which the target gene protein binds or interacts in nature, for example, a molecule in the nucleus or cytoplasm of a cell which expresses the target gene protein. The target gene target molecule can be a non-target gene molecule or the target gene protein or polypeptide. The target, for example, can be a second intracellular protein which has catalytic activity, a protein which naturally binds to the target gene, or a protein which facilitates the association of DNA with the target gene.

Determining the ability of the target gene protein to bind to or interact with the target gene target molecule can be accomplished by one of the methods described above for determining direct binding. In a preferred embodiment, determining the ability of the target gene protein to bind to or interact with the target gene target molecule can be accomplished by determining the activity of the target molecule or detecting a cellular response, for example, cell survival or cell proliferation in the presence of a chemotherapeutic drug.

In yet another embodiment, an assay of the present invention is a cell-free assay comprising contacting the target gene protein or biologically active portion thereof with a test compound and determining the ability of the test compound to bind to the target gene protein or biologically active portion thereof. Binding of the test compound to the target gene protein can be determined either directly or indirectly as described above. In a preferred embodiment, the assay includes contacting the target gene protein or biologically active portion thereof with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or biologically active portion thereof as compared to the known compound.

In another embodiment, an assay is a cell-free assay comprising contacting the target gene protein or biologically active portion thereof with a test compound and determining the ability of the test compound to modulate (e.g., stimulate or inhibit) the activity of the target gene protein or biologically active portion thereof. Determining the ability of the test compound to modulate the activity of the target gene can be accomplished, for example, by determining the ability of the target gene protein to bind to the target gene target molecule by one of the methods described above for determining direct binding. In an alternative embodiment, determining the ability of the test compound to modulate the activity of the target gene can be accomplished by determining the ability of the target gene protein further modulate the target gene target molecule. For example, the catalytic/enzymatic activity of the target molecule on an appropriate substrate can be determined as previously described.

In yet another embodiment, the cell-free assay comprises contacting the target gene protein or biologically active portion thereof with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the target gene protein to preferentially bind to or modulate the activity of the target gene target molecule.

The cell-free assays of the present invention are amenable to use of both native and variant forms (e.g., peptide fragments and fusion proteins) of the target gene. In the case of cell-free assays comprising a hydrophobic form of the target gene, it may be desirable to utilize a solubilizing agent such that the hydrophobic form of the target gene is maintained in solution. Examples of such solubilizing agents include nonionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the target gene or its target molecule to facilitate separation of complexed from uncomplexed forms of one or both of the proteins, as well as to accommodate automation of the assay. Binding of a test compound to the target gene, or interaction of the target gene with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/target gene fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or the target gene protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of the target gene binding or activity determined using standard techniques.

Other techniques for immobilizing proteins on matrices can also be used in the screening assays of the invention. For example, either the target gene or its target molecule can be immobilized utilizing conjugation of biotin and streptavidin. Biotinylated target gene or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the target gene or target molecules but which do not interfere with binding of the target gene protein to its target molecule can be derivatized to the wells of the plate, and unbound target or the target gene trapped in the wells by antibody conjugation. Methods for detecting such complexes, in addition to those described above for the GST-immobilized complexes, include immunodetection of complexes using antibodies reactive with the target gene or target molecule, as well as enzyme-linked assays which rely on detecting an enzymatic activity associated with the target gene or target molecule.

In another embodiment, modulators of the target gene expression are identified in a method in which a cell is contacted with a candidate compound and the expression of the target gene (mRNA or protein, or the copy number of the target gene) in the cell is determined. The level of expression of the target gene in the presence of the candidate compound is compared to the level of expression of the target gene in the absence of the candidate compound. The candidate compound can then be identified as a modulator of the target gene expression based on this comparison. For example, when expression of the target gene mRNA or protein is greater (statistically significantly greater) in the presence of the candidate compound than in its absence, the candidate compound is identified as a stimulator of the target gene mRNA or protein expression. Alternatively, when expression of the target gene mRNA or protein is less (statistically significantly less) in the presence of the candidate compound than in its absence, the candidate compound is identified as an inhibitor of the target gene mRNA or protein expression. The level of the target gene mRNA or protein expression in the cells, or the number of the target gene copies per cell can be determined by methods described herein for detecting the target gene genomic DNA, mRNA, or protein.

Target gene proteins can be used as "bait proteins" in a two-hybrid assay or three hybrid assay (see, e.g., U.S. Pat. No. 5,283,317; Zervos et al. (1993) Cell 72:223-232; Madura et al. (1993) J. Biol. Chem. 268:12046-12054; Bartel et al.

(1993) Dio/Techniques 14:920-924; Iwabuchi et al. (1993) Oncogene 8:1693-1696; and WO94/10300), to identify other proteins, which bind to or interact with the target gene ("target gene-binding proteins" or "target gene-bp") and modulate the target gene activity.

The two-hybrid system is based on the modular nature of most transcription factors, which consist of separable DNA-binding and activation domains. Briefly, the assay utilizes two different DNA constructs. In one construct, the gene that codes for the target gene is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming the target gene-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the target gene.

This invention further pertains to novel agents identified by the above-described screening assays and uses thereof for treatments as described herein.

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the target gene protein and/or nucleic acid expression as well as the target gene activity, in the context of a biological sample (e.g., blood, serum, cells, tissue) to thereby determine whether an individual is afflicted with a disease or disorder, or is at risk of developing a disorder, associated with aberrant target gene expression or activity (e.g., altered drug resistance). The invention also provides for prognostic (or predictive) assays for determining whether an individual is at risk of developing a disorder associated with the target gene protein, nucleic acid expression or activity (e.g., altered drug resistance). For example, mutations in the target gene can be assayed in a biological sample. Such assays can be used for prognostic or predictive purpose to thereby prophylactically treat an individual prior to the onset of a disorder characterized by or associated with the target gene protein, nucleic acid expression or activity. For example, because megakaryocyte production is inhibited where the target gene is expressed at a higher level in cells than normal, expression of the target gene can be used as an indicator of diminished megakaryocyte production.

Another aspect of the invention provides methods for determining the target gene protein, nucleic acid expression or the target gene activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Diagnostic Assays

The invention provides a method of assessing expression, especially undesirable expression, of a cellular target gene. Undesirable (e.g., excessive) expression may indicate the presence, persistence or reappearance of reduced megakaryocyte production in an individual's tissue (e.g. spleen or bone marrow). More generally, aberrant expression may indicate the occurrence of a deleterious or disease-associated phenotype contributed to by the target gene.

An exemplary method for detecting the presence or absence of the target gene in a biological sample involves obtaining a biological sample (preferably from a body site implicated in a possible diagnosis of diseased or malignant tissue) from a test subject and contacting the biological sample with a compound or an agent capable of detecting the target gene protein or nucleic acid (e.g., mRNA, genomic DNA) that encodes the target gene protein such that the presence of the target gene is detected in the biological sample. The presence and/or relative abundance of the target gene indicates aberrant or undesirable expression of a cellular the target gene, and correlates with the occurrence in situ of reduced megakaryocytes in the periphery.

A preferred agent for detecting the target gene mRNA or genomic DNA is a labeled nucleic acid probe capable of hybridizing to the target gene mRNA or genomic DNA. The nucleic acid probe can be, for example, a full-length the target gene nucleic acid, or a portion thereof, such as an oligonucleotide of at least 15, 30, 50, 100, 250 or 500 nucleotides in length and sufficient to specifically hybridize under stringent conditions to the target gene mRNA or genomic DNA. Other suitable probes for use in the diagnostic assays of the invention are described herein.

A preferred agent for detecting the target gene protein is an antibody capable of binding to the target gene protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect the target gene mRNA, protein, or genomic DNA in a biological sample in vitro as well as in vivo. For example, in vitro techniques for detection of the target gene mRNA include Northern hybridizations and in situ hybridizations. In vitro techniques for detection of the target gene protein include enzyme linked immunosorbent assays (ELISAs), Western blots, immunoprecipitations and immunofluorescence. In vitro techniques for detection of the target gene genomic DNA include Southern hybridizations.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting the target gene protein, mRNA, or genomic DNA, such that the presence of the target gene protein, mRNA or genomic DNA is detected in the biological sample, and comparing the presence of the target gene protein, mRNA or genomic DNA in the control sample with the presence of the target gene protein, mRNA or genomic DNA in the test sample.

The invention also encompasses kits for detecting the presence of the target gene in a biological sample (a test sample). Such kits can be used to determine if a subject is suffering from or is at increased risk of developing a disorder associated with aberrant expression of the target gene (e.g., the presence of a drug resistance cancer). For example, the kit can comprise a labeled compound or agent capable of detecting the target gene protein or mRNA in a biological sample and means for determining the amount of the target gene in the sample (e.g., an anti-target gene antibody or an oligonucleotide probe which binds to DNA encoding the target gene, e.g. Kits may also include instruction for observing that the tested subject is suffering from or is at risk of developing a disorder associated with aberrant expression of the target gene if the amount of the target gene protein or mRNA is above or below a normal level.

For antibody-based kits, the kit may comprise, for example: (1) a first antibody (e.g., attached to a solid support) which binds to the target gene protein; and, optionally, (2) a second, different antibody which binds to the target gene protein or the first antibody and is conjugated to a detectable agent.

For oligonucleotide-based kits, the kit may comprise, for example: (1) a oligonucleotide, e.g., a detectably labelled oligonucleotide, which hybridizes to the target gene nucleic acid sequence or (2) a pair of primers useful for amplifying the target gene nucleic acid molecule;

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the target gene.

Pharmacogenomics

Agents, or modulators which have a stimulatory or inhibitory effect on the target gene activity (e.g., SHIP) as identified by a screening assay can be administered to individuals to treat (prophylactically or therapeutically) disorders (e.g., anemias) associated with aberrant target gene activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of the target gene protein, expression of the target gene nucleic acid, or mutation content of the target genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2): 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

Thus, the activity of the target gene protein, expression of the target gene nucleic acid, or mutation content of the target genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with the target gene modulator, such as a modulator identified by one of the exemplary screening assays described herein.

Monitoring of Effects During Clinical Trials

Monitoring the influence of agents (e.g., drugs, compounds) on the expression or activity of the target gene (e.g., the ability to modulate the SHIP phenotype of a cell) can be applied not only in basic drug screening, but also in clinical trials. For example, the effectiveness of an agent determined by a screening assay to decrease the target gene expression, protein levels, or downregulate the target gene activity, can be monitored in clinical trails of subjects exhibiting increased target gene expression, protein levels, or upregulated target gene activity.

Alternatively, the effectiveness of an agent determined by a screening assay to increase the target gene expression, protein levels, or upregulate target gene activity (e.g., to decrease megakaryocyte production), can be monitored in clinical trials of compounds designed to increase the target gene expression, protein levels, or upregulate target gene activity. In such clinical trials, the expression or activity of the target gene and, preferably, other genes that have been implicated in, for example, a cellular proliferation disorder, can be used as a "read out" or markers of the drug resistance of a particular cell.

For example, and not by way of limitation, genes, including the target gene, that are modulated in cells by treatment with an agent (e.g., compound, drug or small molecule) which modulates the target gene activity (e.g., identified in a screening assay) can be identified. Thus, to study the effect of agents on cellular proliferation disorders, for example, in a clinical trial, cells can be isolated and RNA prepared and analyzed for the levels of expression of the target gene and other genes implicated in the disorder. The levels of gene expression (i.e., a gene expression pattern) can be quantified by Northern blot analysis or RT-PCR, or as is otherwise known in the art, or alternatively by measuring the amount of protein produced, by one of the methods as described herein, or by measuring the levels of activity of the target gene or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of the target gene protein, mRNA, or genomic DNA in the preadministration sample; (iii) obtaining one or more post-administration samples from the subject; (iv) detecting the level of expression or activity of the target gene protein, mRNA, or genomic DNA in the post-administration samples; (v) comparing the level of expression or activity of the target gene protein, mRNA, or genomic DNA in the pre-administration sample with the target gene protein, mRNA, or genomic DNA in the post administration sample or samples; and (vi) altering the administration of the agent to the subject accordingly. For example, increased administration of the agent may be desirable to decrease the expression or activity of the target gene to lower levels than detected, i.e., to increase the effectiveness of the agent.

Methods of Treatment

The present invention provides for both prophylactic and therapeutic methods of treating a subject at risk of (or susceptible to) a disorder or having a disorder associated with aberrant target gene expression or activity. Such disorders include various human anemias and those in need of bone marrow transplants.

Prophylactic Methods

In one aspect, the invention provides a method for preventing in a subject, a disease or condition associated with an aberrant target gene expression or activity (e.g., the development of drug resistance), by administering to the subject an agent which modulates the target gene expression. Subjects at risk for a condition which is caused or contributed to by aberrant target gene expression or activity can be identified by, for example, any or a combination of diagnostic or prognostic assays as is known in the art. Administration of a prophylactic agent can occur prior to the manifestation of symptoms characteristic of target gene aberrancy, such that a disease or disorder is prevented or, alternatively, delayed in its progression. For example, administration of a prophylatic agent to a patient in need of a bone marrow transplant may prevent or delay the development of platelet production dropping below a critical threshold. Depending on the type of the target gene aberrancy, for example, the target gene agonist or the target gene antagonist agent can be used for treating the subject. The appropriate agent can be determined based on screening assays described herein.

Therapeutic Methods

Another aspect of the invention pertains to methods of modulating the target gene expression or activity for therapeutic purposes. For example, the effectiveness of a bone marrow transplant is "potentiated" (enhanced) by increasing megakaryocyte production. The modulation of expression of the target gene disclosed in the method of the invention involves contacting a cell with an agent that modulates one or more of the activities of the target gene protein activity associated with the cell. An agent that modulates the target gene protein activity can be an agent as described herein, such as a nucleic acid or a protein, a naturally-occurring cognate ligand of the target gene protein, a peptide, the target gene peptidomimetic, or other small molecule. In one embodiment, the agent stimulates one or more of the biological activities of the target gene protein. Examples of such stimulatory agents include active the target gene protein and a nucleic acid molecule encoding the target gene that has been introduced into the cell. In another embodiment, the agent inhibits one or more of the biological activities of the target gene protein. Examples of such inhibitory agents include antisense target gene nucleic acid molecules and anti-target gene antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of the target gene protein or nucleic acid molecule. In one embodiment, the method involves administering an agent, or combination of agents that modulates (e.g., upregulates or downregulates) the target gene expression or activity. In another embodiment, the method involves administering the target gene protein or nucleic acid molecule as therapy to compensate for reduced or aberrant target gene expression or activity.

For example, in one embodiment, the method involves administering a desired drug to an individual with a cell population expressing relatively high target gene levels, and coadministering an inhibitor of the target gene expression or activity. The administration and coadministration steps can be carried out concurrently or in any order, and can be separated by a time interval sufficient to allow uptake of either compound by the cells to be eradicated. For example, an antisense pharmaceutical composition (or a cocktail composition comprising an the target gene antisense oligonucleotide in combination with one or more other antisense oligonucleotides) can be administered to the individual sufficiently in advance of administration of the drug to allow the antisense composition to permeate the individual's tissues, especially tissue comprising the transformed cells to be eradicated; to be internalized by transformed cells; and to disrupt the target gene expression and/or protein production.

Inhibition of the target gene activity is desirable in situations in which the target gene is abnormally upregulated and/or in which decreased target gene activity is likely to have a beneficial effect, e.g., increasing megakaryocyte production in the tissue of patient. Conversely, stimulation of the target gene activity is desirable in situations in which the target gene is abnormally downregulated and/or in which increased the target gene activity is likely to have a beneficial effect, e.g., in decreasing megakaryocyte production.

This invention is further illustrated by the following examples which should not be construed as limiting. The contents of all references, patents and published patent applications cited throughout this application are hereby incorporated by reference.

Example I

As shown in FIG. 1, SHIP1-deficiency increases the number of megakaryocytes (CD41 +c-kit−) and megakaryocyte progenitors (CD41 +c-kit+) in the hematopoietic compartment. Bone marrow, spleen and blood cells were stained for CD41, c-kit and a Lin panel (CD3, CD4, CD8, B220, Mac1, Gr1, Terr119). CD41 versus c-kit contour plots are shown after gating on Lin− cells in the indicated tissue. Increases in megakaryocyte progenitors (CD41 +c-kit+) are evident in the bone marrow and spleen of the SHIP-deficient animal.

Figure 3:
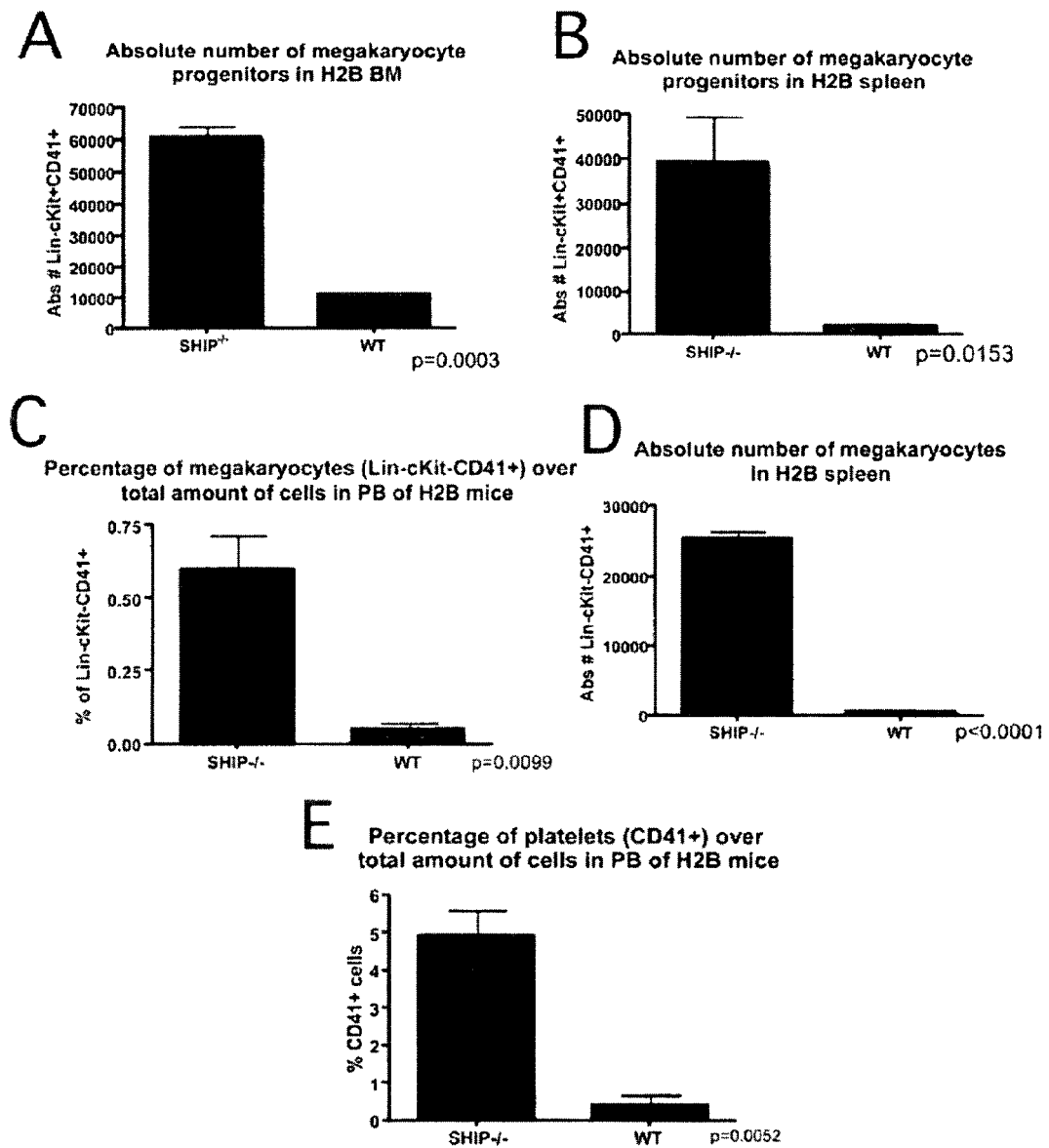
FIG. 3. Statistical analysis of increased megakaryocyte progenitors, megakaryocytes and platelets in SHIP-deficient (SHIP−/−) mice.

Increased numbers of megakaryocytes (CD41 +c-kit−) are found in the spleen and blood of the SHIP-deficient animal. Multiple SHIP1−/− and WT littermates were analyzed and the statistical significance of these increases is shown in FIG. 3.

Example II

Figure 2:
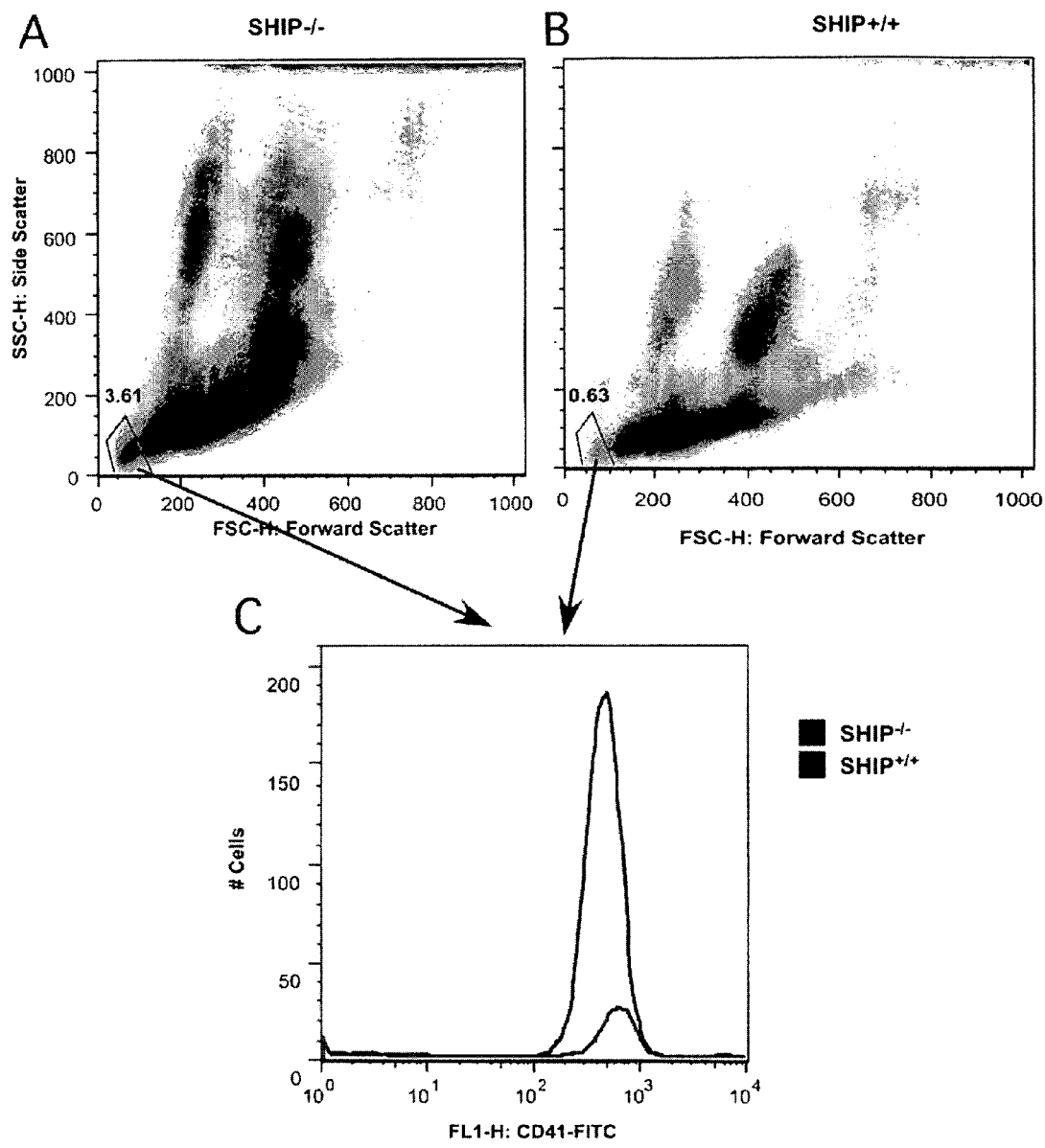
FIG. 2. SHIP1-deficiency increases the number of circulating platelets.

Referring now to FIG. 2, SHIP1-deficiency increases the number of circulating platelets. Fluorescence-Activated Cell Sorter (FACS) analysis of peripheral blood cells stained with anti-CD41 (megakaryocyte/platelet marker) from SHIP1-deficient (SHIP−/−) (A) and normal (SHIP+/+) (B) mice. A, B. Platelets were initially quantitated based on their size (small forward and obtuse light scattering cells indicated by blue gates in A and B). C. The platelet identity of these small light scatter cells was confirmed by their expression of the CD41 marker.

Example III

Statistical analysis of increased megakaryocyte progenitors, megakaryocytes and platelets in SHIP-deficient (SHIP−/−) mice are depicted in FIG. 3. A, B. Absolute numbers of megakaryocyte progenitors as defined by CD41 +c-kit+ expression (see FIG. 1) were significantly increased in sites of primary (bone marrow, BM) and extramedullary (spleen) sites of hematopoiesis in SHIP1-deficient mice as compared to normal mice (WT). C, D. Absolute megakaryocyte numbers are increased in peripheral hematopoietic tissues (spleen and blood) of SHIP1-deficient mice (see FIG. 1). E. Platelet numbers are increased in the blood of SHIP1-deficient mice relative to normal mice (see FIG. 2). All p-values were determined by a two-tailed Students' T-test. A p-value of less than 0.05 indicates the increased numbers for the above cell populations in SHIP-deficient mice (SHIP−/−) are highly significant as compared to normal mice.

Example IV

Figure 4:
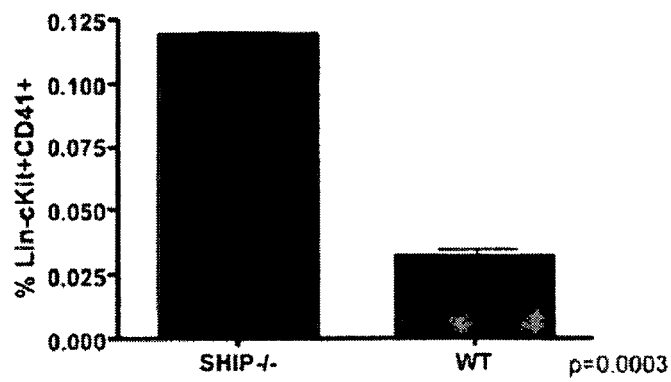
FIG. 4. SHIP1-deficiency increases the frequency of megakaryocyte progenitors and megakaryocytes in the hematopoietic compartment.
Figure 4:
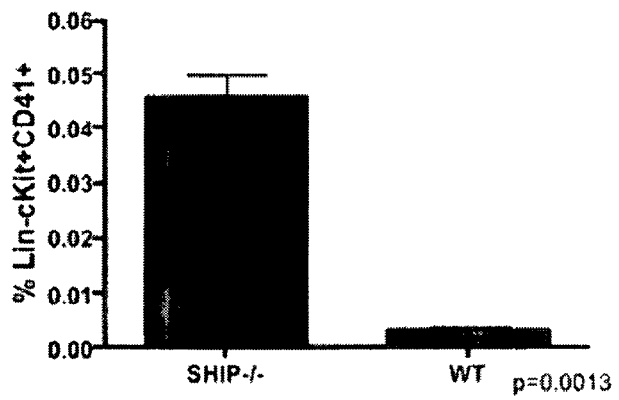
Figure 4:
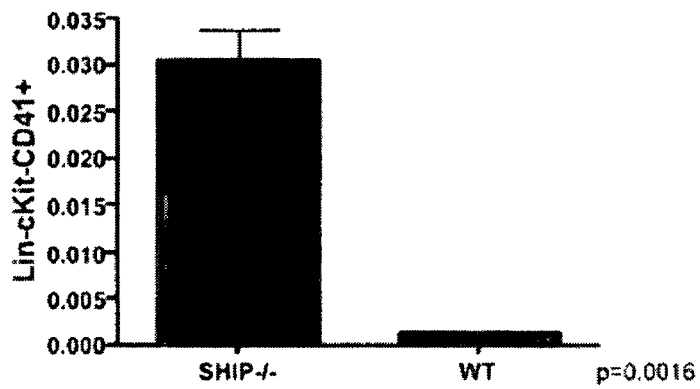

FIG. 4 shows SHIP1-deficiency increases the frequency of megakaryocyte progenitors and megakaryocytes in the hematopoietic compartment [BM and blood (see FIG. 3)]. All p values were determined by a two-tailed Students' T-test. A p-value of less than 0.05 indicates the increased numbers for the above cell populations in SHIP-deficient mice (SHIP−/−) are highly significant as compared to normal WT littermates.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be the to fall therebetween. Now that the invention has been described,

---

What is claimed is:

1. A method of increasing the yield of megakaryocyte progenitors from a human patient, ex vivo, comprising the steps of:
   harvesting target cells comprising megakaryocyte progenitors from a patient;
   inhibiting SH2-domain-containing inositol 5'-phosphatase (SHIP) expression in the megakaryocyte progenitors using RNA interference; and contacting the megakaryocyte progenitors with cellular growth factors, wherein the number of megakaryocyte progenitors is thereby increased.

2. The method of claim 1, wherein the method further comprises the step of reinfusing the megakaryocyte progenitors into the patient after the contacting step.

3. The method of claim 1, wherein the cellular growth factors are human cellular growth factors.

* * * * *

UNITED STATES PATENT AND TRADEMARK OFFICE
CERTIFICATE OF CORRECTION

| | | |
|---|---|---|
| PATENT NO. | : 7,807,646 B1 | Page 1 of 1 |
| APPLICATION NO. | : 10/904667 | |
| DATED | : October 5, 2010 | |
| INVENTOR(S) | : William G. Kerr, Caroline Desponts and Lia Elena Perez | |

It is certified that error appears in the above-identified patent and that said Letters Patent is hereby corrected as shown below:

Column 1,
Lines 7-10, "The subject matter of this application has been supported by research grants from the Leukemia and Lymphoma Society of America and the National Institutes of Health under grant numbers HL072523 and CA087989." should read
-- This invention was made with government support under grant numbers HL072523 and CA087989 awarded by the Leukemia and Lymphoma Society of America and the National Institutes of Health.--.
Line 10, "Accordingly, the" should read --The--.
Line 11, "this invention." should read --the invention.--.

Column 16,
Line 6, "include active the target gene protein" should read --include the target gene protein--.
Line 7, "target gene that" should read --target gene protein that--.
Line 34, "comprising an the" should read --comprising the--.
Line 46, "tissue of patient" should read --tissue of a patient--.

Signed and Sealed this
Eleventh Day of January, 2011

David J. Kappos
*Director of the United States Patent and Trademark Office*